US011510612B2

United States Patent
Ghannam et al.

(10) Patent No.: US 11,510,612 B2
(45) Date of Patent: Nov. 29, 2022

(54) SYSTEMS AND METHODS FOR DETECTING ALERTNESS OF AN OCCUPANT OF A VEHICLE

(71) Applicant: Ford Global Technologies, LLC, Dearborn, MI (US)

(72) Inventors: Mahmoud Yousef Ghannam, Canton, MI (US); Adil Nizam Siddiqui, Farmington Hills, MI (US); Justin Bennie, Sterling Heights, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 332 days.

(21) Appl. No.: 16/696,066

(22) Filed: Nov. 26, 2019

(65) Prior Publication Data

US 2021/0153806 A1 May 27, 2021

(51) Int. Cl.
*A61B 5/00* (2006.01)
*A61B 5/18* (2006.01)
(Continued)

(52) U.S. Cl.
CPC .......... *A61B 5/4809* (2013.01); *A61B 5/0205* (2013.01); *A61B 5/18* (2013.01);
(Continued)

(58) Field of Classification Search
CPC ....... A61B 3/10; A61B 5/0002; A61B 5/0205; A61B 5/021; A61B 5/024; A61B 5/08;
(Continued)

(56) References Cited

U.S. PATENT DOCUMENTS

| 5,689,241 A | 11/1997 | Clarke, Sr. et al. |
| 2020/0057487 A1* | 2/2020 | Sicconi ................... G06T 7/174 |
| 2020/0130706 A1* | 4/2020 | Rakshit ................. B60W 50/14 |

FOREIGN PATENT DOCUMENTS

WO  2016132848 A1  8/2016

OTHER PUBLICATIONS

Pereira et al. Lagophthalmos. Semin Ophthalmol. May 2010. 25(3):72-78 (Year: 2010).*

(Continued)

*Primary Examiner* — Mallika D Fairchild
*Assistant Examiner* — Shreya Anjaria
(74) *Attorney, Agent, or Firm* — Frank Lollo; Eversheds Sutherland (US) LLP

(57) ABSTRACT

Exemplary embodiments described in this disclosure are generally directed to systems and methods for detecting alertness of a driver of a vehicle. In one exemplary method, a driver alertness detection system determines whether a driver of a vehicle is susceptible to lagophthalmos. If the driver is susceptible to lagophthalmos, the driver alertness detection system may evaluate an alertness state of the driver by disregarding an eyelid status of the driver and monitoring biometrics of the driver such as, a heart rate and/or a breathing pattern. Alternatively, the driver alertness detection system may evaluate an alertness state of the driver by placing a higher priority on the biometrics of the driver than on the eyelid status. However, if the driver is not susceptible to lagophthalmos, the driver alertness detection system evaluates the alertness state by placing a higher priority on the eyelid status than on the biometrics of the driver.

20 Claims, 5 Drawing Sheets

(51) Int. Cl.
    *A61B 5/0205* (2006.01)
    *A61B 5/024* (2006.01)
    *A61B 5/08* (2006.01)
    *A61B 5/11* (2006.01)
    *G16H 40/63* (2018.01)
    *B60W 40/08* (2012.01)

(52) U.S. Cl.
    CPC ............ *A61B 5/681* (2013.01); *A61B 5/6893* (2013.01); *A61B 5/6898* (2013.01); *A61B 5/7275* (2013.01); *A61B 5/7282* (2013.01); *B60W 40/08* (2013.01); *G16H 40/63* (2018.01); *A61B 5/0002* (2013.01); *A61B 5/024* (2013.01); *A61B 5/0816* (2013.01); *A61B 5/1103* (2013.01); *B60W 2040/0818* (2013.01); *B60W 2040/0872* (2013.01)

(58) Field of Classification Search
    CPC ....... A61B 5/1103; A61B 5/18; A61B 5/4809; A61B 5/681; A61B 5/6893; A61B 5/6898; A61B 5/7275; A61B 5/7282; A61B 2503/22; B60W 40/08; B60W 40/09; B60W 2040/0818; B60W 2040/0827; B60W 2040/0872; B60W 2040/043; B60W 2040/221; B60W 2040/225; B60W 2556/10; G08B 21/0211; G08B 21/06; G16H 10/60; G16H 20/00; G16H 40/63; G16H 40/67
    See application file for complete search history.

(56) References Cited

OTHER PUBLICATIONS

Taub, Eric. A., "Sleepy Behind the Wheel? Some Cars Can Tell," The New York Times, Aug. 28, 2019 (3 pages).
Ueno, Hiroshi et al., "Development of Drowsiness Detection System," Vehicle Research Laboratory, Nissan Research Center, Nisson Motor Co., Ltd., 1994 Vehicle Navigation & Information Systems Conference Proceedings (6 pages).

* cited by examiner

SYSTEMS AND METHODS FOR DETECTING ALERTNESS OF AN OCCUPANT OF A VEHICLE

FIELD OF THE DISCLOSURE

This disclosure generally relates to vehicles, and more particularly relates to systems and methods for detecting alertness of a driver (or a passenger) of a vehicle.

BACKGROUND

A major concern in traffic safety is driver behavior, particularly distracted driving and drowsiness. Vehicle manufacturers have addressed such types of driver behaviors by offering driving monitoring systems (DSMs). A typical driving monitoring system monitors various physical characteristics of a driver in order to continuously assess his/her alertness. One among the various physical characteristics that are monitored is a condition of the driver's eyes in order to identify drowsiness. Typically, the eyelids of a sleepy driver tend to be droopy, partially closed, or fully closed. When such a condition is detected, the driving monitoring system may provide an audible alarm and/or provide a vibration in the steering wheel of the vehicle so as to awaken the driver.

While this procedure may be effective in many cases, some drivers may suffer from a medical condition known as lagophthalmos. A person suffering from lagophthalmos typically falls asleep with eyes wide open, both during the day when in a sitting position or at night when in bed (nocturnal lagophthalmos). Some people may be born with lagophthalmos and some others may be afflicted with lagophthalmos due to injury or due to factors such as Bells' palsy, Graves' disease, paralytic stroke, or tumor.

A conventional driving monitoring system that relies largely on detecting driver alertness based on monitoring a driver's eyes may mistakenly diagnose a driver suffering from lagophthalmos as being fully alert even though the driver may be asleep. It is therefore desirable to provide solutions that can monitor driver alertness taking into consideration that a driver may have lagophthalmos.

BRIEF DESCRIPTION OF THE DRAWINGS

A detailed description is set forth below with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

Figure 1:
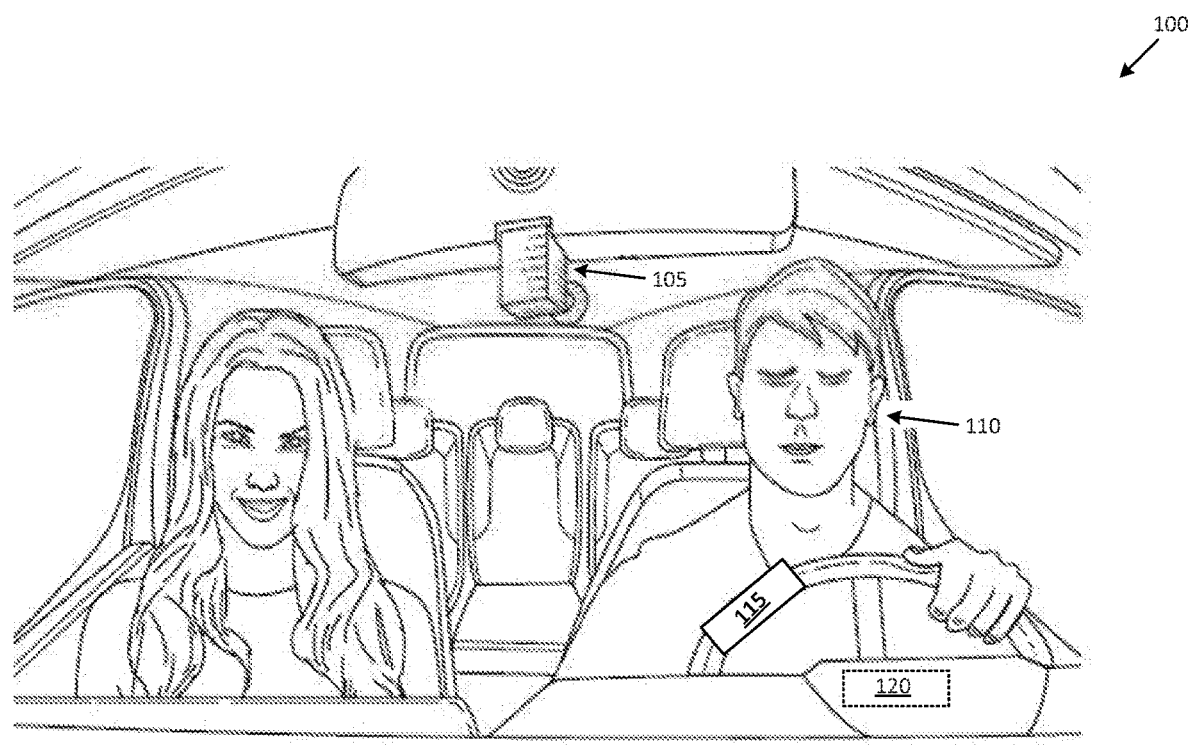
FIG. 1 illustrates an exemplary embodiment of a driver alertness detection system in accordance with the disclosure for detecting an alertness state of a driver.

In terms of a general overview, certain embodiments described in this disclosure are generally directed to systems and methods for detecting alertness of a driver of a vehicle. A driver alertness detection system is used to determine whether a driver of a vehicle is susceptible to lagophthalmos. When the driver is susceptible to lagophthalmos, the driver alertness detection system may evaluate an alertness state of the driver by disregarding an eyelid status of the driver and monitoring one or more biometrics of the driver such as, for example, a heart rate or a breathing pattern. In another exemplary method, the driver alertness detection system may evaluate an alertness state of the driver by placing a higher priority on the biometrics of the driver than on the eyelid status of the driver. However, when the driver is not susceptible to lagophthalmos, the driver alertness detection system may evaluate the alertness state of the driver by using a standard procedure that involves placing a higher priority on the eyelid status of the driver than on the biometrics of the driver.

Illustrative Embodiments

The disclosure will be described more fully hereinafter with reference to the accompanying drawings, in which exemplary embodiments of the disclosure are shown. This disclosure may, however, be embodied in many different forms and should not be construed as limited to the exemplary embodiments set forth herein. It will be apparent to persons skilled in the relevant art that various changes in form and detail can be made to various embodiments without departing from the spirit and scope of the present disclosure. Thus, the breadth and scope of the present disclosure should not be limited by any of the above-described exemplary embodiments but should be defined only in accordance with the following claims and their equivalents. The description below has been presented for the purposes of illustration and is not intended to be exhaustive or to be limited to the precise form disclosed. It should be understood that alternate implementations may be used in any combination desired to form additional hybrid implementations of the present disclosure. For example, any of the functionality described with respect to a particular device or component may be performed by another device or component. Furthermore, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments.

Certain words and phrases are used herein solely for convenience and such words and terms should be interpreted as referring to various objects and actions that are generally understood in various forms and equivalencies by persons of ordinary skill in the art. For example, word "driver" as used herein may be equally applicable to a passenger of a vehicle or in some cases, to a person who is requesting a ride in a ride-share vehicle. Words such as "person" or "occupant"

may be used in some cases to indicate a driver, a passenger, or a potential passenger of a vehicle. The word "vehicle" as used in this disclosure can pertain to any one of various types of vehicles such as cars, vans, sports utility vehicles, trucks, electric vehicles, gasoline vehicles, hybrid vehicles, and autonomous vehicles. The word "biometrics" as used in this disclosure generally refers to various parameters of a human body that may be used to identify a physical condition, such as a sleeping condition or an alert condition. The word "information" as used herein can pertain to data, signals, communications (for example, messages) and other such items that can be processed by processing circuitry for carrying out various operations. Words such as "having," "suffering," "condition," and "afflicted," may be used in an interchangeable manner and generally denote that a physical condition such as lagophthalmos is associated with an individual being referred to. The word "standard" as used herein generally refers to an action that is known in popular practice. It should also be understood that the word "example" as used herein is intended to be non-exclusionary and non-limiting in nature. More particularly, the word "exemplary" as used herein indicates one among several examples, and it should be understood that no undue emphasis or preference is being directed to the particular example being described.

FIG. 1 illustrates an exemplary embodiment of a driver alertness detection system 100 in accordance with the disclosure for detecting a driver 110 who is asleep at the wheel of a vehicle. The driver alertness detection system 100 may be implemented in a variety of ways and can include various type of sensors. In one exemplary implementation, the driver alertness detection system 100 can include an imaging apparatus 105, a facial recognition system 120, and one or more biometric sensors (such as an exemplary biometric sensor 115).

The imaging apparatus 105 can be mounted on any of various parts of the vehicle having a field of view that encompasses at least a portion of a face of the driver 110, particularly the eyes of the driver 110. The imaging apparatus 105 in this example illustration is mounted upon a rear-view mirror of the vehicle and is arranged to capture one or more images of the eyes of the driver 110. In some cases, the imaging apparatus 105 can be a video camera that captures real-time video of at least the eyes of the driver 110. In some other cases, the imaging apparatus 105 can be a digital camera that captures digital images of at least the eyes of the driver 110. The digital images may be captured on a repetitive basis, an intermittent basis, and/or a random basis. The real-time video and/or digital images are conveyed to a processing circuit (not shown) of the driver alertness detection system 100 for processing in order to detect an eyelid status of the driver 110. An eyelid status, such as, for example, an open condition, a drooping condition, a partially closed condition, or a fully closed condition, can provide an indication of an alertness state of the driver 110.

The facial recognition system 120 can be mounted on any of various parts of the vehicle having a field of view that encompasses a face of the driver 110. The facial recognition system 120 in this example illustration is mounted upon an instrument panel of the vehicle and is arranged to capture images of the face of the driver 110 (digital images and/or video). The images may be conveyed to the processing circuit of the driver alertness detection system 100 for processing in order to analyze various facial features of the driver 110. Facial features such as a drooping mouth, a slack jaw, and/or an angular orientation can provide an indication of an alertness state of the driver 110.

The biometric sensor 115 can include one or more of various types of devices that may be mounted on various parts of the vehicle and used to detect various types of physical conditions of the driver 110 for purposes of evaluating an alertness state of the driver 110. The biometric sensor 115 in this example illustration can be a pressure sensor that senses a placement of the hands of the driver 110 upon the steering wheel and/or an intensity of a hand grip of the driver 110 upon the steering wheel. In another example embodiment, the biometric sensor 115 can be a body sensor that is provided in a driver seat occupied by the driver 110. The body sensor may measure various biometric parameters of the driver 110, such as, for example, blood pressure, heart rate, brainwaves, and breathing pattern. The body sensor may incorporate various types of technologies, such as, for example, infra-red technology, green light technology, radio-frequency (RF) technology, and/or pressure transducer technology.

One example of the use of infra-red technology is for temperature measurements and distance measurements. One example of the use of green-light technology is in fitness monitoring devices such as a Fitbit® activity tracker where a pair of LEDs shine green light that measures minute changes in the color characteristics of blood flowing through a human body. The color characteristics typically vary in correspondence to a blood pumping action of the heart and can be used to determine parameters such as pulse rate and heartbeat.

In the exemplary scenario illustrated in FIG. 1, the processing circuit of the driver alertness detection system 100 may process the information provided by the imaging apparatus 105, the facial recognition system 120, and/or the biometric sensor 115 over a period of time (which can be referred to as a sampling period), and conclude that there is a high probability that the driver 110 is asleep at the wheel. Processing the information provided by the various sources such as the imaging apparatus 105, the facial recognition system 120, and/or the biometric sensor 115 may include applying various levels of priorities. In one exemplary implementation, the application of priorities may be carried out by applying weights to the information received from the various sources. Typically, continuous eyelid closure over an extended period of is a good indicator that a person is asleep. An intermittent eyelid closure may indicate that a person is drowsy. Heart rate and breathing patterns can also indicate an alertness state of a person. However, such states can be prone to certain ambiguities among different individuals. For example, some physical parameters (such as heart rate, breathing pattern, and/or blood pressure) of an athletic individual may be different than that of a sedentary individual.

Consequently, the processing circuit of the driver alertness detection system 100 may apply a greater weight to the eyelid status of the driver 110 than to the biometric measurements. For example, the driver alertness detection system 100 may apply a numerical weight of 8 (out of 10) for signals received from the imaging apparatus 105 and/or the facial recognition system 120, and use this weighting to evaluate the eyelid status of the driver 110. The driver alertness detection system 100 may apply a lower weight (5, for example) to the signals received from the biometric sensor 115 for evaluating other physical conditions of the driver 110 to determine the alertness state of the driver 110. Such a weighting scheme where the eyelid status is used as primary indicator of alertness may be effective when the driver 110 does not suffer from lagophthalmos. However, this approach may be ineffective when the driver 110 has lagophthalmos, because the eyelids of the driver 110 may remain open even though the driver 110 has fallen asleep at the wheel.

Figure 2:
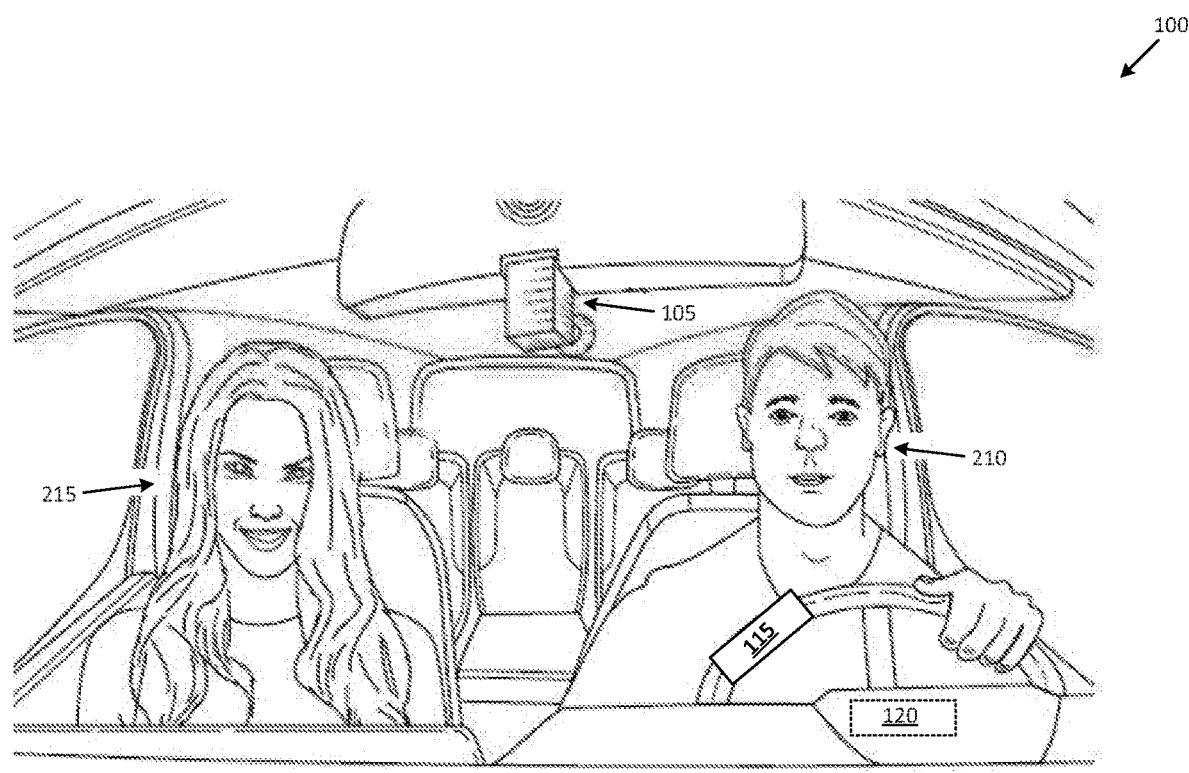
FIG. 2 illustrates an exemplary embodiment of the driver alertness detection system in accordance with the disclosure for detecting an alertness state of a driver afflicted with lagophthalmos.

FIG. 2 illustrates an exemplary embodiment of the driver alertness detection system 100 configured to detect an alertness state of an occupant of a vehicle when afflicted with lagophthalmos. The occupant of the vehicle can either be a driver 210 or a passenger 215 of the vehicle. Though the following description is directed at the driver 210, it must be understood that the description is equally applicable to any occupant of a vehicle. For example, in some instances, the vehicle can be an autonomous vehicle and all the occupants of the autonomous vehicle are passengers. In such a situation, particularly when the autonomous vehicle is a ride share vehicle and the passengers do not know each other, it may be disconcerting for a first passenger to see a second passenger sitting with eyes wide open and not responding in a manner that is expected of a person who is awake. The first passenger may be unaware that the second passenger is afflicted with lagophthalmos.

In an exemplary scenario that is illustrated in FIG. 1, the driver alertness detection system 100 may process signals received from the biometric sensor 115 and conclude that there is a high probability that the driver 210 is in a sleeping state or a drowsy state. However, due to the lagophthalmos condition of the driver 210 and the resulting wide-open eyes, the signals received from the imaging apparatus 105 and/or the facial recognition system 120 may provide an eyelid status indicative of the driver 210 being awake. Upon encountering such a conflicting situation, the driver alertness detection system 100 can initiate a procedure to determine if the driver 210 suffers from lagophthalmos. In one exemplary implementation, the driver alertness detection system 100 may fetch medical records of the driver 210 to do so. In another exemplary implementation, the driver alertness detection system 100 may execute a learning procedure to determine whether the driver 210 suffers from lagophthalmos.

If one or both of the procedures indicate that the driver 210 suffers from lagophthalmos, the driver alertness detection system 100 evaluates the alertness state of the driver 210 by placing a higher priority on signals received from the biometric sensor 115 than on signals received from devices such as the imaging apparatus 105 and/or the facial recognition system 120 used to determine an eyelid status of the driver 210. For example, the driver alertness detection system 100 may apply a numerical weight of 8 (out of 10) for signals received from the biometric sensor 115 and a lower weight (5, for example) to the signals received from the imaging apparatus 105 and/or the facial recognition system 120 when evaluating the alertness state of the driver 110.

In accordance with a second implementation of this exemplary embodiment, the driver alertness detection system 100 evaluates the alertness state of the driver 210 by disregarding signals received from devices such as the imaging apparatus 105 and/or the facial recognition system 120, and only process signals received from the biometric sensor 115. For example, the driver alertness detection system 100 may evaluate the alertness state of the driver 210 based on a heart rate or a breathing pattern of the driver 210 and disregard an eyelid status of the driver 210 in view of the driver 210 having lagophthalmos.

Figure 3A:
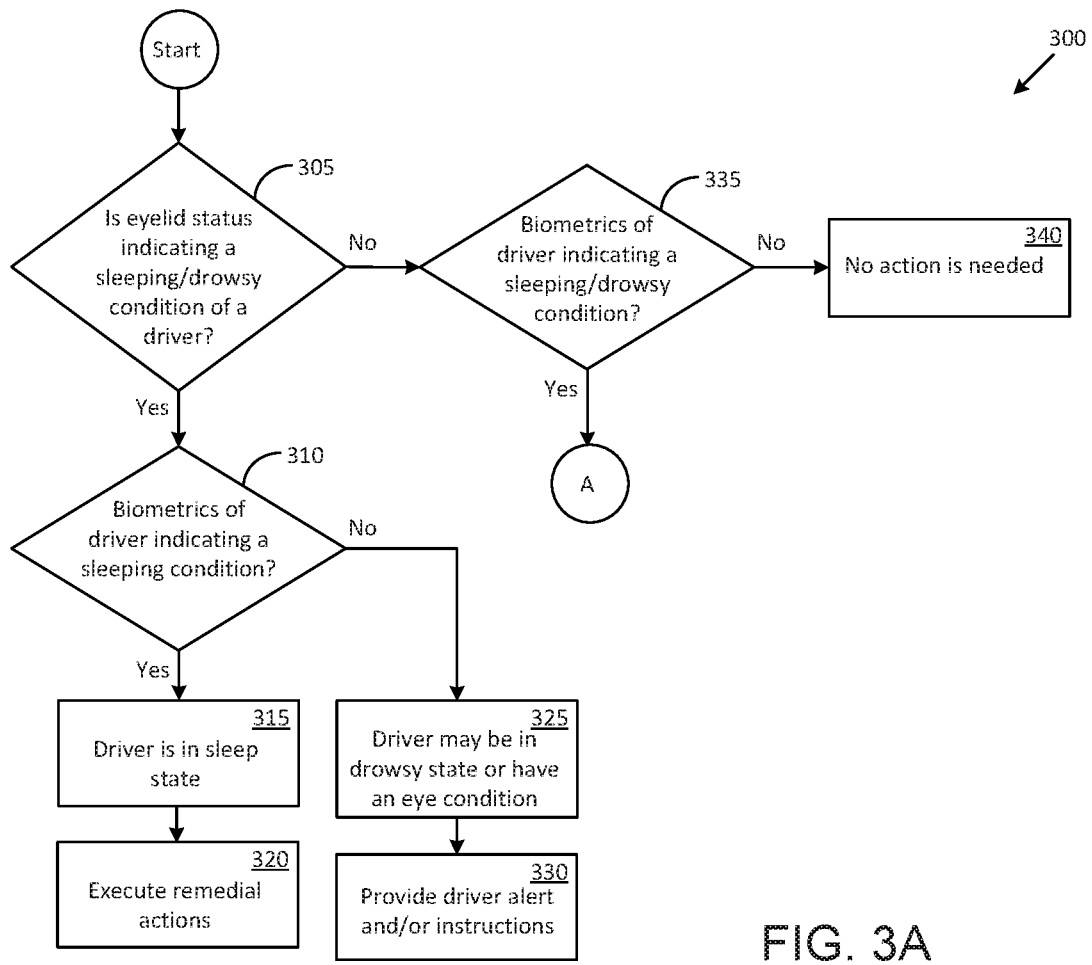
FIGS. 3A-3B shows a flowchart of a method of operation of a driver alertness detection system in accordance with the disclosure.
Figure 3B:
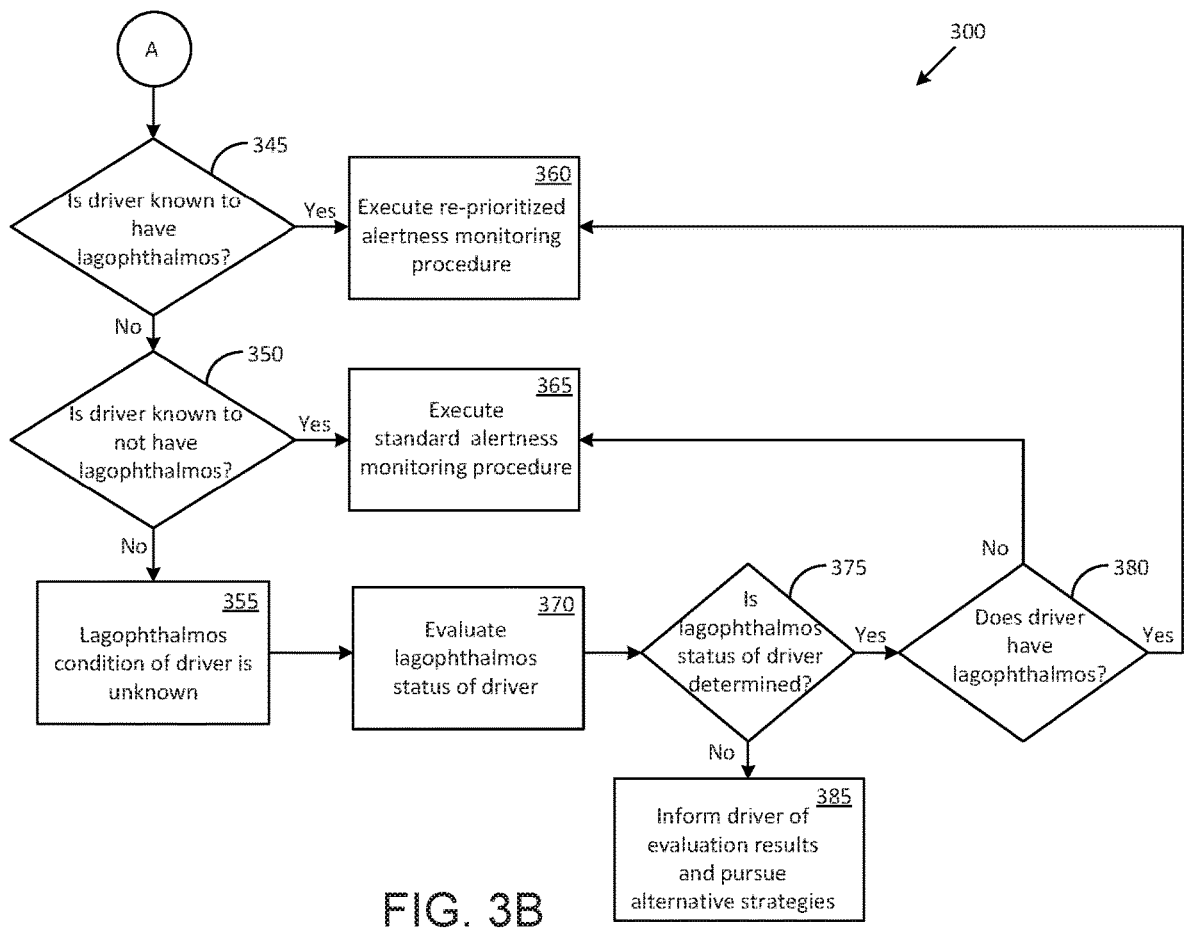

FIGS. 3A-3B shows a flowchart 300 of a method of operation of a driver alertness detection system in accordance with the disclosure. The flowchart 300 illustrates a sequence of operations that can be implemented in hardware, software, or a combination thereof. In the context of software, the operations represent computer-executable instructions stored on one or more non-transitory computer-readable media (such as a memory 410 that is described below). The computer-executable instructions may be executed by one or more processors (such as a processor 405 that is described below), to perform the recited operations. Generally, computer-executable instructions include routines, programs, objects, components, data structures, and the like that perform particular functions or implement particular abstract data types. The order in which the operations are described is not intended to be construed as a limitation, and any number of the described operations may be carried out in a different order, omitted, combined in any order, and/or carried out in parallel. Some or all of the operations described in the flowchart 300 may be carried out by using an application such as a driver alertness detection system module 411 contained in a memory 410 as described below using FIG. 4.

At block 305, a determination may be made by a driver alertness detection system whether an eyelid status of a driver of a vehicle indicates a sleepy or drowsy condition. For example, a processor may process images received from the imaging apparatus 105 and/or the facial recognition system 120 and conclude that the driver is asleep, based on detecting that the eyelids of the driver have remained closed for a period of time (for over a minute, for example). As another example, the processor may process images received from the imaging apparatus 105 and/or the facial recognition system 120 and conclude that the driver is drowsy, based on detecting that the eyelids of the driver close occasionally or flutter intermittently over a period of time (for 3 minutes, for example).

If the eyelid status of the driver indicates a sleepy or drowsy condition, at block 310, a determination is made whether biometric signals received from one or more biometric sensors, such as the biometric sensor 115, indicate a sleeping condition. For example, the processor may process signals from a biometric sensor that monitors breathing activity of the driver and detect a sleeping breathing pattern. As another example, the processor may process signals from a biometric sensor that monitors brain activity of the driver and detect a sleeping brainwave pattern.

If the biometrics of the driver confirm the sleepy or drowsy condition that is indicated by the eyelid status of the driver, at block 315, the processor draws a conclusion that the driver is in a sleep state.

At block 320, remedial actions may be taken. For example, the driver alertness detection system 100 may communicate with an infotainment system in the vehicle to emit an audible signal (beeps, tones, music, etc.) for waking the driver. When the vehicle is an autonomous vehicle, further action may be taken if the driver does not respond to the audible signal. For example, the autonomous vehicle may slow down and come to a halt on the side of a road if the driver does not wake up after repeated attempts.

If, at block 310, the biometric signals received from the biometric sensor such as the biometric sensor 115 do not indicate a sleeping condition even though the eyelid status indicates a sleeping or drowsy condition, at block 325, the processor may conclude that the driver is either drowsy or may have an eye problem.

Consequently, at block 330, the driver alertness detection system 100 may display on a display screen of the infotainment system in the vehicle, a message that recommends the driver to take a break or drink coffee. In some cases, the processor may advice the driver to seek medical assistance to treat an eye condition such as redness, dryness, allergies etc.

Turning back to block 305, if the eyelid status of the driver indicates a sleepy or drowsy condition, at block 335, a determination is made whether biometric signals received from one or more biometric sensors indicate a sleeping condition. For example, the processor may detect a sleeping breathing pattern and/or a sleeping brainwave pattern that provides an indication that the driver is either sleeping or is drowsy. If the biometric sensors indicate that the driver is not in a sleeping/drowsy condition, thereby confirming the eyelid status (at block 305) that is indicative of the driver not being asleep or drowsy, at block 340, no further action is taken by the driver alertness detection system 100. However, if the indication provided by the biometric sensors indicate that the driver is sleepy or drowsy, thereby contradicting the eyelid status (at block 305) that is indicative of the driver not being asleep or drowsy, at block 345 (FIG. 3B), a determination is made whether the driver is known to have lagophthalmos. The operations that are carried out to make the determination may also be applicable to a passenger of the vehicle or a person requesting a ride in a ride share vehicle. As such, words such as "person" or "occupant" may be used below when subject matter is applicable to the driver and the passenger. Some actions carried out with respect to a passenger may be different than those carried out with respect to a driver, because the passenger is not directly involved with driving operations of the vehicle. In these instances, the word "passenger" or "driver" may be used to provide clarity.

Furthermore, in some cases, a person may request a ride in a ride share vehicle, which can be either an autonomous vehicle or a driver-operated vehicle. In such cases, the actions described below may be carried out prior to the person becoming an occupant of the ride share vehicle (by a ride-share service provider, for example).

At least four different scenarios may be applicable when making this determination. A first scenario pertains to a person having lagophthalmos and being aware that he/she has lagophthalmos. A second scenario pertains to a person having lagophthalmos and being unaware that he/she has lagophthalmos. A third scenario pertains to a person not having lagophthalmos and being aware that he/she does not have lagophthalmos. A fourth scenario pertains to a person not having lagophthalmos and being unaware that he/she does not have lagophthalmos.

If the first scenario is applicable, at block 360, a re-prioritized alertness monitoring procedure may be executed. The re-prioritized alertness monitoring procedure refers to a modification of a standard alertness monitoring procedure. The standard alertness monitoring procedure, which is applicable to an occupant of the vehicle who does not have lagophthalmos, involves applying a higher priority (weighting) to the eyelid status of the person than to biometric factors such as a breathing pattern or a heart rate. Thus, the eyelid status of the occupant becomes the primary criterion for detecting alertness. On the other hand, re-prioritized alertness monitoring procedure involves applying a higher priority (weighting) to biometric factors rather than the eyelid status of the occupant for detecting alertness because the eyelid status of a person suffering from lagophthalmos may be a poor indicator of alertness.

If the first scenario is not applicable, at block 350, a determination is made whether the occupant of the vehicle is known to not have lagophthalmos. If, the third scenario is applicable here (i.e., occupant does not have lagophthalmos and is aware of it), at block 365, the standard alertness monitoring procedure may be executed. If, on the other hand, the second or the fourth scenario is applicable here (occupant is unaware if he/she has or does not have lagophthalmos), at block 355, the processor concludes that a lagophthalmos condition of the occupant of the vehicle is unknown.

At block 370, a lagophthalmos status of the occupant of the vehicle may be evaluated. The evaluation may be carried out in various ways and may be also applicable in the case of a person requesting a ride in a ride share vehicle. In one exemplary embodiment in accordance with the disclosure, a processor that can be a part of the driver alertness detection system 100 obtains a medical history of a person from one or more of various sources. For example, the medical history of the person may be obtained from a server computer that is configured to wirelessly communicate with the driver alertness detection system. As another example, the medical history of the person may be obtained from a database that is a part of the driver alertness detection system 100. As yet another example, the medical history of the person may be obtained from a device such as a fitness bracelet worn by the person.

In another exemplary embodiment in accordance with the disclosure, the processor can generate a medical profile of the occupant of a vehicle based on monitoring and analyzing eyelid status and biometric data of the occupant over a period of time. The period of time can, for example, correspond to multiple trips performed by the occupant in the vehicle. The medical profile of the occupant may lead to a finding that the occupant suffers from lagophthalmos. The finding may be based on the biometric data (such as the heart rate and the breathing pattern of the occupant) indicating a sleeping profile while the eyelid status indicates an awake profile. Alternatively, the medical profile of the occupant may lead to a finding that the occupant does not suffer from lagophthalmos when both the eyelid status and the biometric data indicate a sleeping profile.

At block 375, a determination may be made whether the lagophthalmos status of the person has been determined. If a determination has been made, at block 380, a determination is made whether the person has lagophthalmos. If the person does not have lagophthalmos, the standard alertness monitoring procedure can be executed (block 365). If the person has lagophthalmos and is an occupant of the vehicle, the re-prioritized alertness monitoring procedure can be executed (block 360). In one exemplary case where the occupant of the vehicle is a passenger in the vehicle, the other occupants of the vehicle may be informed of the lagophthalmos condition of the passenger so as to assuage any concerns that the other passengers may have. In another exemplary case, the passenger may be provided an eye mask by a driver of the vehicle or that is provided in a receptacle of the vehicle. The eye mask may be provided in a ride share vehicle, for example, prior to a person entering the vehicle. Appropriate messages (text and/or audio) may be provided via the infotainment system of the vehicle to inform the person about the eye mask. In yet another exemplary case, where the vehicle is an autonomous vehicle, certain actions may be carried out to assist the person suffering from lagophthalmos. These actions may include automatically increasing an amount of window tinting, or repositioning a seat to provide more comfort and/or privacy to the person. A person seeking a ride in a ride-share vehicle and is aware that he/she has lagophthalmos may request a specific type of vehicle or may request privacy with respect to his/her medical condition.

In some cases, at block 375, it may be discovered that the lagophthalmos status of the person is indeterminate. This may occur, for example, if the person has an eye defect and/or other physical characteristics that render the monitoring and analyzing of the eyelid status and the biometric data of the person inconclusive.

When the lagophthalmos status of the person is indeterminate, at block 385, the person may be informed of the inclusive evaluation results. The driver alertness detection system may pursue alternative strategies to resolve the indeterminate lagophthalmos status of the person. For example, driver alertness detection system may request input from the driver via the infotainment system of the vehicle and/or urge the driver to periodically confirm his/her alertness by performing various tasks when seated in the vehicle. Some exemplary tasks can include touching certain components in the vehicle, operating certain components in the vehicle, uttering certain words into a microphone coupled to the infotainment system.

Figure 4:
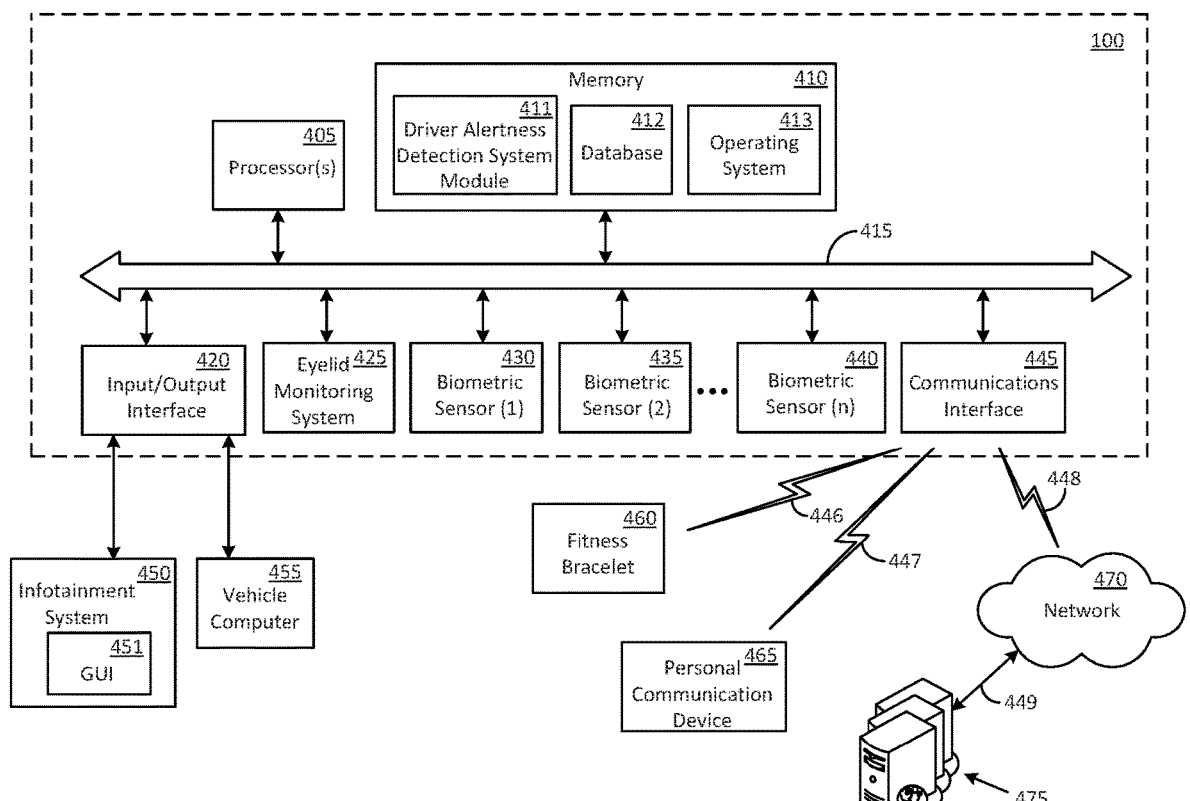
FIG. 4 shows some exemplary components that may be included in a driver alertness detection system in accordance with the disclosure.

FIG. 4 shows some exemplary components that may be included in the driver alertness detection system 100 in accordance with the disclosure. In this example configuration, the driver alertness detection system 100 may include a processor 405, an input/output (I/O) interface 420, an eyelid monitoring system 425, one or more biometric sensors such as biometric sensor (1) 430, biometric sensor (2) 435, and biometric sensor (n) 440 (n≥1), a communications interface 445, and a memory 410. The various components of the driver alertness detection system 100 can be communicatively coupled to each other via a bus 415.

The bus 415 can be implemented using one or more of various wired and/or wireless technologies. For example, the bus can be a vehicle bus that uses a controller area network (CAN) bus protocol, a Media Oriented Systems Transport (MOST) bus protocol, and/or a CAN flexible data (CAN-FD) bus protocol. Some or all portions of the bus may also be implemented using wireless technologies such as Bluetooth®, Zigbee®, or near-field-communications (NFC), cellular, Wi-Fi, Wi-Fi direct, machine-to-machine communication, and/or man-to-machine communication to accommodate communications between the driver alertness detection system 100 and devices such as, for example, an infotainment system 450, a fitness bracelet 460, and/or a personal communication device 465.

The memory 410, which is one example of a non-transitory computer-readable medium, may be used to store an operating system (OS) 413 and one or more code modules such as a driver alertness detection system module 411. The code modules can be provided in the form of computer-executable instructions that are executed by the processor 405 for performing various operations in accordance with the disclosure. For example, the processor 405 can execute the driver alertness detection system module 411 to perform various actions such as the ones described above with reference to FIGS. 3A-3B.

The memory 410 can also include a database 412 that may be used to store information such as, for example, a medical history, a medical profile, physical attributes, medical conditions, and personal preferences of a driver of a vehicle. The database 412 may also be used to store information, such as medical information provided by the driver via a graphical user interface (GUI) 451 of the infotainment system 450.

The input/output (I/O) interface 420 can include various types of wired and/or wireless circuitry to allow the driver alertness detection system 100 to communicate with the infotainment system 450 and a vehicle computer 455. In some implementations where the bus 415 is a vehicle bus, the input/output (I/O) interface 420 may be omitted and the infotainment system 450 and/or the vehicle computer 455 may be coupled directly to the bus 415. The vehicle computer 455 may perform various functions of the vehicle such as controlling engine operations (fuel injection, speed control, emissions control, braking, etc.), managing climate controls (air conditioning, heating etc.), activating airbags, and issuing warnings (check engine light, bulb failure, low tire pressure, vehicle in blind spot, etc.).

The eyelid monitoring system 425 can include one or more of various types of devices such as the imaging apparatus 105 and the facial recognition system 120 described above. The biometric sensors can include, for example, a pressure sensor and/or a body sensor. The pressure sensor can be used to detect placement of the hands of a driver upon a steering wheel of a vehicle and/or an intensity of a hand grip upon the steering wheel. The body sensor may be used to measure various biometric parameters of a driver, such as, for example, blood pressure, heart rate, brainwaves, and breathing pattern.

The communications interface 445 provides for wireless communications between the driver alertness detection system 100 and various devices such as the fitness bracelet 460, the personal communications device 465, and a server computer 475 (via a network 470). The fitness bracelet 460, which can include devices such as a Fitbit® activity tracker or an Apple® Watch, can provide information that may be used by the driver alertness detection system 100 to determine an alertness condition of a driver. The fitness bracelet 460 may communicate with the driver alertness detection system 100 via a wireless communication link 446 that can incorporate technologies such as Bluetooth®, Zigbee®, or near-field-communications (NFC), cellular, Wi-Fi, Wi-Fi direct, and machine-to-machine communication.

The information provided by the fitness bracelet 460 may, for example, indicate to the driver alertness detection system 100 that the driver did not have adequate sleep the previous night, or that the driver has had excessive physical exertion over the past few hours prior to getting into the vehicle (walking up a flight of stairs, bending down to pick up multiple loads, high heart rate associated with exertion, etc.). Such actions may lead to the driver having a sleeping condition or drowsiness when at the wheel of the vehicle.

The personal communication device 465, which can be a smartphone for example, can provide information that may be used by the driver alertness detection system 100 to determine an alertness condition of a driver. For example, a fitness application executed in the smartphone may provide information to the driver alertness detection system 100 that the driver has undergone excessive physical exertion over the past few hours prior to getting into the vehicle. A global positioning system (GPS) application executed in the smartphone may provide walking information to indicate that the driver has walked over a certain distance prior to getting into the vehicle. The fitness bracelet 460 may communicate with the driver alertness detection system 100 via a wireless communication link 447 that can incorporate technologies such as Bluetooth®, Zigbee®, or near-field-communications (NFC), cellular, Wi-Fi, Wi-Fi direct, machine-to-machine communication, and/or man-to-machine communication.

The server computer 475 may communicate with the driver alertness detection system 100 via the network 470. Information provided by the server computer 475 to the driver alertness detection system 100 can include a medical history of the driver, and/or information pertaining to websites visited by the driver. The information pertaining to the websites may indicate that the driver has communicated with help groups, support groups, social media sites, and medical-related sites for various reasons associated with lagophthalmos.

The network 470 may include any one, or a combination of networks, such as a local area network (LAN), a wide area network (WAN), a telephone network, a cellular network, a cable network, a wireless network, and/or private/public networks such as the Internet. For example, the network 470 may support communication technologies such as TCP/IP, Bluetooth, cellular, near-field communication (NFC), Wi-Fi, Wi-Fi direct, machine-to-machine communication, and/or man-to-machine communication.

Some or all portions of the wireless communication link 448 that supports communications between the driver alertness detection system 100 and a communication device such as a router, for example, that may be included in the network 470, can be implemented using various types of wireless technologies such as Bluetooth®, Zigbee®, or near-field-communications (NFC), cellular, Wi-Fi, Wi-Fi direct, machine-to-machine communication, man-to-machine communication, and/or a vehicle-to-everything (V2X) communication. The communication link 449 that supports communications between the server computer 475 and the network 470 may incorporate one or more of various types of wired and/or wireless technologies used for communications.

In the above disclosure, reference has been made to the accompanying drawings, which form a part hereof, which illustrate specific implementations in which the present disclosure may be practiced. It is understood that other implementations may be utilized, and structural changes may be made without departing from the scope of the present disclosure. References in the specification to "one embodiment," "an embodiment," "an example embodiment," "an exemplary embodiment," "exemplary implementation," etc., indicate that the embodiment or implementation described may include a particular feature, structure, or characteristic, but every embodiment or implementation may not necessarily include the particular feature, structure, or characteristic. Moreover, such phrases are not necessarily referring to the same embodiment or implementation. Further, when a particular feature, structure, or characteristic is described in connection with an embodiment or implementation, one skilled in the art will recognize such feature, structure, or characteristic in connection with other embodiments or implementations whether or not explicitly described.

Implementations of the systems, apparatuses, devices, and methods disclosed herein may comprise or utilize one or more devices that include hardware, such as, for example, one or more processors and system memory, as discussed herein. An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or any combination of hardwired or wireless) to a computer, the computer properly views the connection as a transmission medium. Transmission media can include a network and/or data links, which can be used to carry desired program code means in the form of computer-executable instructions or data structures and which can be accessed by a general purpose or special purpose computer. Combinations of the above should also be included within the scope of non-transitory computer-readable media.

Computer-executable instructions comprise, for example, instructions and data which, when executed at a processor, cause the processor to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

A memory device such as the memory 410, can include any one memory element or a combination of volatile memory elements (e.g., random access memory (RAM, such as DRAM, SRAM, SDRAM, etc.)) and non-volatile memory elements (e.g., ROM, hard drive, tape, CDROM, etc.). Moreover, the memory device may incorporate electronic, magnetic, optical, and/or other types of storage media. In the context of this document, a "non-transitory computer-readable medium" can be, for example but not limited to, an electronic, magnetic, optical, electromagnetic, infrared, or semiconductor system, apparatus, or device. More specific examples (a non-exhaustive list) of the computer-readable medium would include the following: a portable computer diskette (magnetic), a random-access memory (RAM) (electronic), a read-only memory (ROM) (electronic), an erasable programmable read-only memory (EPROM, EEPROM, or Flash memory) (electronic), and a portable compact disc read-only memory (CD ROM) (optical). Note that the computer-readable medium could even be paper or another suitable medium upon which the program is printed, since the program can be electronically captured, for instance, via optical scanning of the paper or other medium, then compiled, interpreted or otherwise processed in a suitable manner if necessary, and then stored in a computer memory.

Those skilled in the art will appreciate that the present disclosure may be practiced in network computing environments with many types of computer system configurations, including in-dash vehicle computers, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by any combination of hardwired and wireless data links) through a network, both perform tasks. In a distributed system environment, program modules may be located in both the local and remote memory storage devices.

Further, where appropriate, the functions described herein can be performed in one or more of hardware, software, firmware, digital components, or analog components. For example, one or more application specific integrated circuits (ASICs) can be programmed to carry out one or more of the systems and procedures described herein. Certain terms are used throughout the description, and claims refer to particular system components. As one skilled in the art will appreciate, components may be referred to by different names. This document does not intend to distinguish between components that differ in name, but not function.

At least some embodiments of the present disclosure have been directed to computer program products comprising such logic (e.g., in the form of software) stored on any computer-usable medium. Such software, when executed in one or more data processing devices, causes a device to operate as described herein.

While various embodiments of the present disclosure have been described above, it should be understood that they have been presented by way of example only, and not limitation. It will be apparent to persons skilled in the relevant art that various changes in form and detail can be made therein without departing from the spirit and scope of the present disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the present disclosure to the precise form disclosed. Many modifications and variations are possible in light of the above teaching. Further, it should be noted that any or all of the aforementioned alternate implementations may be used in any combination desired to form additional hybrid implementations of the present disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. A method comprising:
   determining, by a vehicle, that an occupant of the vehicle is susceptible to lagophthalmos;
   determining a first alertness weight associated with eyelid status data associated with the occupant and a second alertness weight associated with biometric data associated with the occupant, wherein the first alertness weight is provided a first value that is less than a second value associated with the second alertness weight based on the determination that the occupant is susceptible to lagophthalmos, wherein the eyelid status data and the biometric data are obtained by one or more sensors of the vehicle, and wherein the vehicle is an autonomous vehicle;
   determining, based on the eyelid status data, the biometric data, the first alertness weight, and the second alertness weight, that the occupant is experiencing a sleepy or drowsy condition; and
   causing, by the vehicle and based on the determination that the occupant is experiencing a sleepy or drowsy condition, the vehicle to automatically pull over to a side of a road.

2. The method of claim 1, wherein the occupant of the vehicle is a driver of the vehicle and the biometric data of the driver includes a heart rate of the driver and a breathing pattern of the driver, the method further comprising:
   determining, that a second driver is insusceptible to lagophthalmos; and
   determining a third alertness weight associated with eyelid status data associated with the occupant and a fourth alertness weight associated with biometric data associated with the occupant, wherein the third alertness weight is provided a third value that is greater than a fourth value associated with the fourth alertness weight based on the determination that the occupant is susceptible to lagophthalmos.

3. The method of claim 1, wherein determining whether the occupant is susceptible to lagophthalmos comprises:
   obtaining, by the vehicle, at least a portion of a medical history of the occupant.

4. The method of claim 1, wherein determining whether the occupant is susceptible to lagophthalmos comprises:
   obtaining input from the occupant.

5. The method of claim 1, wherein determining whether the occupant is susceptible to lagophthalmos comprises:
   generating a medical profile of the occupant based on monitoring and analyzing a heart rate, a breathing pattern, or an eyelid status of the occupant over a period of time.

6. The method of claim 5, wherein the occupant of the vehicle is a driver of the vehicle and the period of time corresponds to multiple trips performed by the driver in the vehicle or when the driver is lying down in a bed.

7. A system comprising:
   a memory that stores computer-executable instructions; and
   a processor configured to access the memory and execute the computer-executable instructions to at least:
   determine by a vehicle, that an occupant of the vehicle is susceptible to lagophthalmos;
   determine a first alertness weight associated with eyelid status data associated with the occupant and a second alertness weight associated with biometric data associated with the occupant, wherein the first alertness weight is provided a first value that is less than a second value associated with the second alertness weight based on the determination that the occupant is susceptible to lagophthalmos, wherein the eyelid status data and the biometric data are obtained by one or more sensors of the vehicle, and wherein the vehicle is an autonomous vehicle;
   determine, based on the eyelid status data, the biometric data, the first alertness weight, and the second alertness weight, that the occupant is experiencing a sleepy or drowsy condition; and
   cause, by the vehicle and based on the determination that the occupant is experiencing a sleepy or drowsy condition, the vehicle to automatically pull over to a side of a road.

8. The system of claim 7, wherein the occupant of the vehicle is a driver of the vehicle and wherein determining that the driver of the vehicle is insusceptible to lagophthalmos comprises placing the driver in one of at least four categories, the four categories comprising:

a first category wherein the driver of the vehicle has a lagophthalmos affliction and is aware of the lagophthalmos affliction;

a second category wherein the driver of the vehicle has a lagophthalmos affliction and is unaware of the lagophthalmos affliction;

a third category wherein the driver of the vehicle does not have a lagophthalmos affliction and is aware of not having the lagophthalmos affliction; and a fourth category wherein the driver of the vehicle does not have a lagophthalmos affliction and is unaware of not having the lagophthalmos affliction.

9. The system of claim 7, wherein the occupant of the vehicle is a driver of the vehicle and wherein determining that the driver is insusceptible to lagophthalmos comprises at least one of: obtaining, from a database, at least a portion of a medical history of the driver, obtaining input from the driver, or obtaining data from a device.

10. The system of claim 9, wherein the device is at least one of a first monitoring device located in the vehicle or a second monitoring device that is carried by the driver.

11. The system of claim 10, wherein the second monitoring device is one of a smartphone or a health monitoring bracelet.

12. The system of claim 7, wherein the occupant of the vehicle is a driver of the vehicle and wherein determining that the driver is insusceptible to lagophthalmos comprises:
generate a medical profile of the driver based on monitoring and analyzing one or more of a heart rate, a breathing pattern, or an eyelid status of the driver during at least at least one of multiple trips performed by the driver in the vehicle or when the driver is lying down in a bed.

13. A vehicle comprising:
a memory that stores computer-executable instructions; and
a processor configured to access the memory and execute the computer-executable instructions to at least:
determine, by the vehicle, that an occupant of the vehicle is susceptible to lagophthalmos;
determine a first alertness weight associated with eyelid status data associated with the occupant and a second alertness weight associated with biometric data associated with the occupant, wherein the first alertness weight is provided a first value that is less than a second value associated with the second alertness weight based on the determination that the occupant is susceptible to lagophthalmos, wherein the eyelid status data and the biometric data are obtained by one or more sensors of the vehicle, and wherein the vehicle is an autonomous vehicle;
determine, based on the eyelid status data, the biometric data, the first alertness weight, and the second alertness weight, that the occupant is experiencing a sleepy or drowsy condition; and
cause, by the vehicle and based on the determination that the occupant is experiencing a sleepy or drowsy condition, the vehicle to automatically pull over to a side of a road.

14. The vehicle of claim 13, wherein the vehicle is an autonomous vehicle and wherein the processor is configured to access the memory and execute additional computer-executable instructions to at least one of obtain from a database at least a portion of a medical history of the occupant, input from the occupant, or data from a device.

15. The vehicle of claim 14, wherein the device is at least one of a first monitoring device located in the vehicle or a second monitoring device that is carried by the occupant, wherein the second monitoring device is one of a smartphone or a health monitoring bracelet.

16. The vehicle of claim 13, wherein the occupant of the vehicle is a driver of the vehicle and wherein determining that the driver is susceptible to lagophthalmos comprises:
generating a medical profile of the driver based on monitoring and analyzing one or more of a heart rate, a breathing pattern, or an eyelid status of the driver during at least at least one of multiple trips performed by the driver in the vehicle or when the driver is lying down in a bed.

17. The of claim 1, wherein determining whether the occupant is susceptible to lagophthalmos comprises:
determining that the eyelid status data indicates that eyelids of the occupant are open at a first time; and
determining that the biometric data indicates that the occupant is experiencing a sleepy or drowsy condition at the first time.

18. The system of claim 7, wherein determining whether the occupant is insusceptible to lagophthalmos comprises:
determine that the eyelid status data indicates that eyelids of the occupant are closed at a first time; and
determine that the biometric data indicates that the occupant is experiencing a sleepy or drowsy condition at the first time.

19. The vehicle of claim 13, wherein determining whether the occupant is susceptible to lagophthalmos comprises:
determining that the eyelid status data indicates that eyelids of the occupant are open at a first time; and
determining that the biometric data indicates that the occupant is experiencing a sleepy or drowsy condition at the first time.

20. The method of claim 17, further comprising:
determining, based on the biometric data or the eyelid status data, that it is indeterminate if the occupant is susceptible to lagophthalmos;
causing, by the vehicle, to present an indication to the occupant to provide an input;
receiving the input from the occupant; and
determining that the occupant is insusceptible to lagophthalmos based on receiving the input.

* * * * *